United States Patent [19]
Christen et al.

[11] 3,954,012
[45] May 4, 1976

[54] AUTOMATIC SAMPLER APPARATUS

[75] Inventors: Urs Christen; Raymond Ernest Pecsar, both of Walnut Creek; Brent E. Wadsworth, Concord, all of Calif.

[73] Assignee: Varian Associates, Palo Alto, Calif.

[22] Filed: June 3, 1974

[21] Appl. No.: 475,481

Related U.S. Application Data

[62] Division of Ser. No. 337,800, March 5, 1973, abandoned.

[52] U.S. Cl. ............................. 73/422 GC; 73/423 A
[51] Int. Cl.² ............................................. G01N 1/12
[58] Field of Search ................... 73/422 GC, 423 A; 23/253, 259

[56] References Cited
UNITED STATES PATENTS

| | | | |
|---|---|---|---|
| 3,475,964 | 11/1969 | Jenkins | 73/422 GC |
| 3,479,880 | 11/1969 | Mutter | 73/423 A |
| 3,604,269 | 9/1971 | Smith et al. | 73/423 A |
| 3,754,443 | 8/1973 | Harris et al. | 73/423 A |

*Primary Examiner*—S. Clement Swisher
*Attorney, Agent, or Firm*—Stanley Z. Cole; Gerald M. Fisher; John J. Morrissey

[57] ABSTRACT

A system for injecting sample fluids into an analyzer and processing the analysis data is disclosed. The system includes a fluid sample analyzer, a sample storage module for a number of fluid samples, an injection module by which samples are injected into the analyzer, and a control module for governing and sequencing the operation of the system. The storage module houses a plurality of sample-containing trays which can be loaded with samples remote from the system. A gas operated liquid purging system is employed for minimizing the quantity of residual material injected into the analyzer with successive samples, which system operates over a broad range of purging fluid viscosities using excessive amounts of fluid purge material.

12 Claims, 5 Drawing Figures

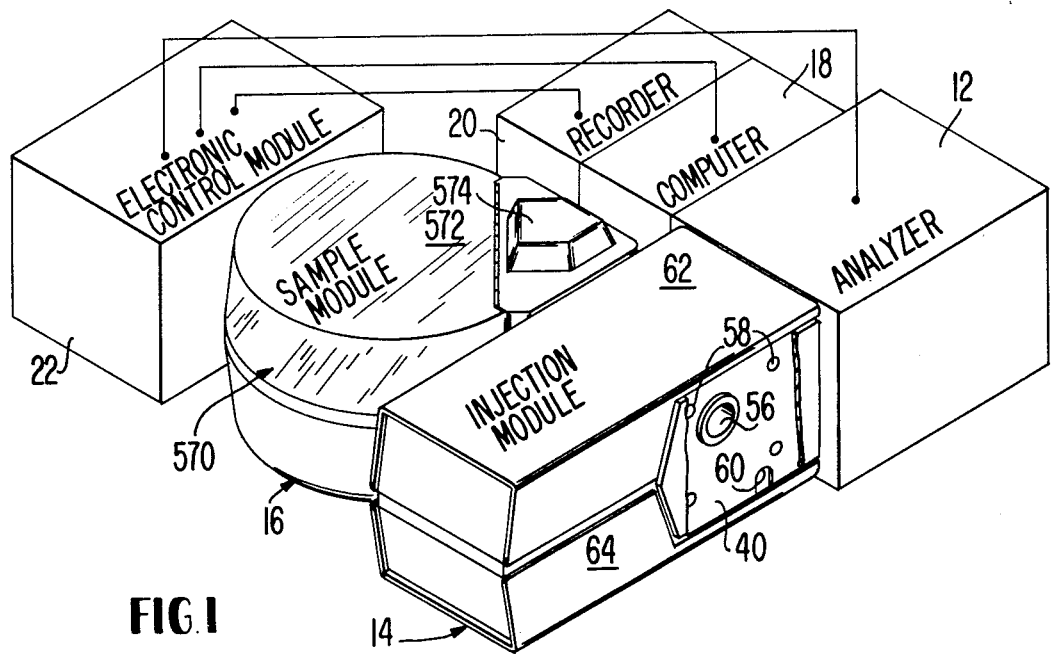
FIG.1
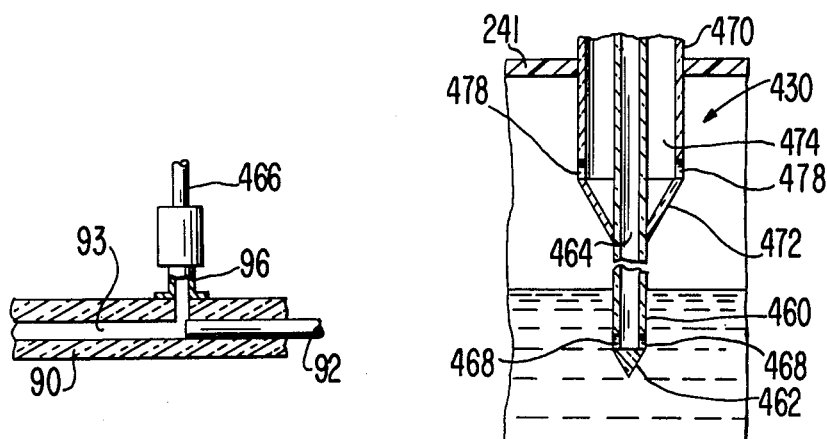
FIG.2
FIG.3

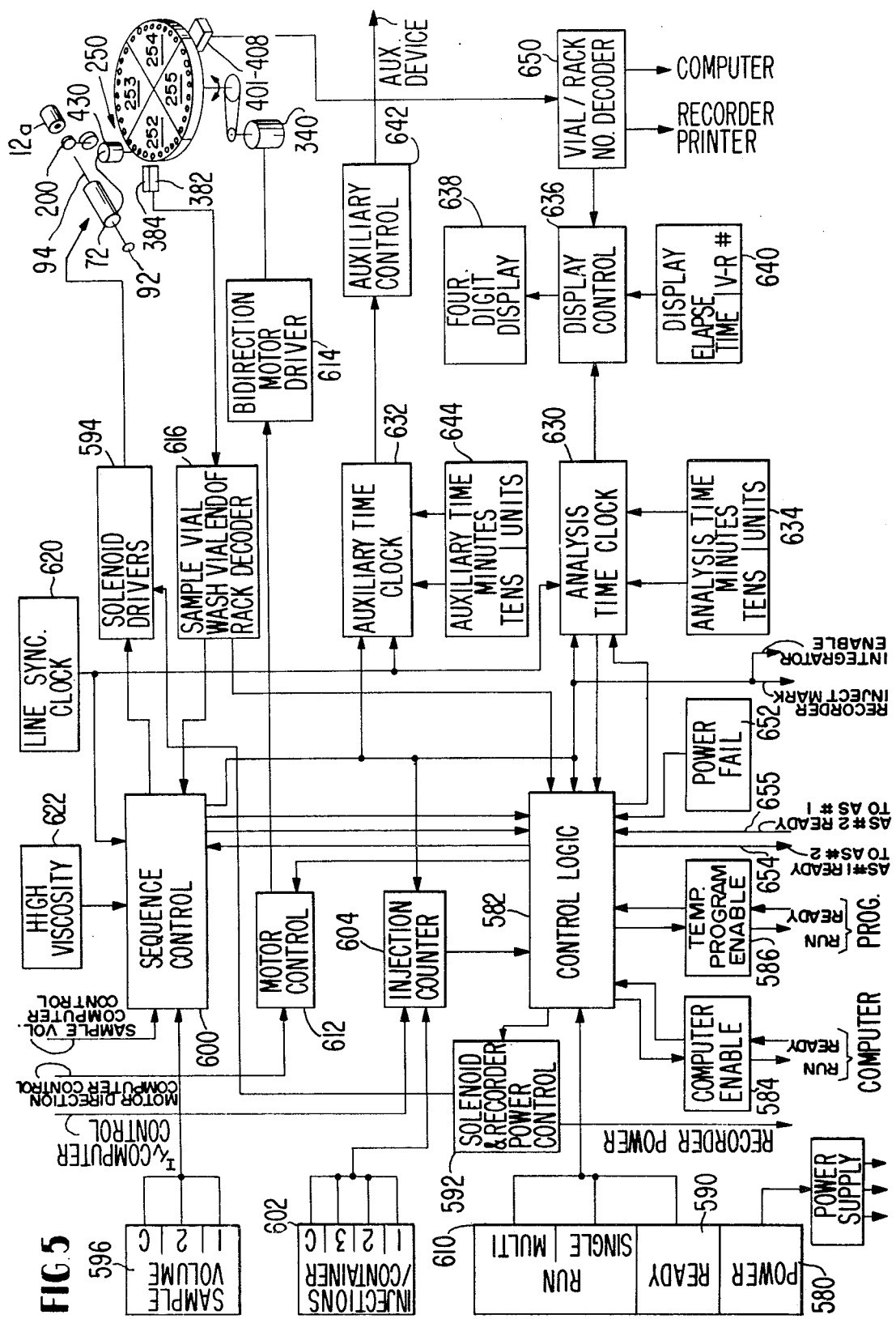

AUTOMATIC SAMPLER APPARATUS

This is a division of application Ser. No. 337,800 filed Mar. 5, 1973, now abandoned.

BACKGROUND OF THE INVENTION

1. Field of the Invention

The present invention relates to the analysis of sample fluids and more particularly relates to systems for controlling the introduction of sample fluids into an analyzer.

2. Prior Art

Systems for suppling fluid samples for analysis by equipment, such as chromatographic analyzers, have been proposed by the prior art. Some prior art systems have employed a syringe for introducing a predetermined quantity of sample fluid into the analyzer equipment. Sample fluids to be analyzed were disposed in separate closed sample containers; and successive individual fluid samples were removed from their containers, supplied to the syringe, and injected into the equipment.

It is imperative in most sample analyses that the sample fluid being analyzed be as free as possible from any type of foreign substance. Accordingly, the injection syringe was required to be thoroughly purged of one sample fluid and/or any residual cleansing solvent before a succeeding sample was placed in the syringe. The syringes employed for sample fluid injection were quite delicate because of the extremely small quantities of sample fluid they handled, e.g. quantities of from 5 – 50 microliters. This made manual operation and purging of the syringes both tedious and time consuming. Furthermore, when large numbers of samples were being successively analyzed, a skilled operator was required to attend the equipment and perform the tedious and repetitive tack of purging and filling the syringe.

In order to increase the speed and efficiency of the analysis of multiple fluid samples, mechanized syringe handling systems were proposed. The purpose of such systems was to reduce the amount of operator time required in connection with the analysis procedures and to reduce equipment failures, e.g. the syringe breakage and damage which inevitably resulted from frequent handling.

The mechanized systems generally consisted of a supporting tray for sample containers and an injection syringe manipulating mechanism which functioned to enable removal of sample fluid from individual containers, injection of the fluid into the analyzer and purging of the syringe. The sample container trays were usually actuatable to index successive sample containers to a location from which fluid was transferred to the syringe.

While the prior art mechanized systems were effective in reducing the amount of operator time required to analyze fluid samples, several problems relating to syringe manipulation and purging remained unsolved.

In some proposals the mechanized syringe purging left undesirably large quantities of foreign materials in the samples which were injected into the analyzers. In one type of system, for example, the syringe plunger was mechanically reciprocated during purging to draw in and expel successive charges of solvent and/or sample fluid prior to injection of that sample fluid into the analyzer.

In another type of system, a side arm syringe was employed and purging was accomplished by retracting the syringe plunger beyond the syringe side arm port, after which solvent and/or sample fluid was pumped through the syringe barrel for a predetermined period of time.

Both of these purging procedures, while preferable to manual purging, left undesirably large quantities of foreign material in the sample fluid injected into the analyzers. In particular, it is discovered that volatile fluids created pump cavitation which resulted in the formation of gas bubbles in the purge fluid. This reduced the purging effectiveness.

In still other proposals, sample liquids were subjected to a predetermined differential gas pressure for a predetermined period of time so that the sample liquid was forced through the injection syringe and associated conduits to effect purging. Because sample fluid viscosity varied widely, these systems were subject to extending too much sample fluid during the purging process when low viscosity fluids were employed, and did not expend adequate quantities of fluid for complete purging of highly viscous samples. In circumstances where highly volatile fluid samples were, the partial pressure of the fluid vapor tended to substantially increase the applied pressure differential and the purge volume was thus difficult to accurately control.

SUMMARY OF THE INVENTION

The present invention provides a new and improved sample analysis method and system wherein sample fluid injection equipment and associated sample flow conduits are purged by a controlled volume of purging fluid so that samples of fluid injected in the apparatus are nearly uniformly pure regardless of differences in sample fluid viscosity and/or volatility; over a large range of differing liquid levels in the solvent or sample containers.

In a preferred and illustrated embodiment of the invention, a sample analysis system is provided which comprises a sample analyzer, preferably a gas chromotograph, a sample injection module by which a sample of fluid to be analyzed is injected into the analyzer, a sample storage module which houses a number of discrete samples of fluid to be analyzed and which supplies sample fluid to the injection module, a sample analysis computer which may be programmed to partially govern operation of the system and to receive raw data from the analyzer concerning the analysis of the given sample of fluid, a recorder which is connected to the analyzer for producing graphic information concerning the analysis of given samples by the analyzer, and an electronic control module which governs operation of the components of the system.

The sample storage module receives a plurality of separate sample storage trays, or racks, in which a number of sample containers may be placed, preferably of the 2 milliliter size. The trays or racks are detachably connected to the storage module and as such can be loaded with samples remote from the analysis system. The trays or racks can be loaded with containers in laboratories and forwarded to the analysis system. The operator of the system thus does not have to load or unload trays, and is not required to account for the identity and location of any given fluid sample.

The sample storage module is detachably connected to the injection module, and sample fluid which is withdrawn from an individual container in the storage module is conducted into the injection module via a sample conduit. The injection module includes a syringe connected to the conduit which injects a predetermined dose of the fluid into the analyzer. Prior to the injection of a sample, the sample conduit and the injection syringe in the module are purged to remove residual fluid from a previous cycle of the system.

An important feature of the invention resides in the purging process by which a predetermined amount of purging energy is provided to the fluid in the storage module so that a controlled quantity of the purging fluid is directed through the sample conduit and injection syringe. In the preferred and illustrated embodiment of the invention, purging fluid (either sample fluid or a solvent) is located in a container which is closed by a septum. A syringe-like dipper tube assembly is advanced into the container through the septum. The dipper tube assembly comprises a first tube which communicates with the injection syringe through the sample conduit and a second tube which is connected with a purging system.

When the dipper tube assembly is advanced into the container, vapor pressure in the container is vented to atmosphere through the purging system dipper tube to produce atmospheric pressure in the container. The purging system is then operated to expose the fluid in the container to a predetermined volume of gas at a predetermined pressure, preferably by discharging an accumulator into the container via the second dipper tube conduit. This creates a pressure differential across the sample extracting dipper tube, the conduit and the injection syringe so that a predetermined quantity of the fluid is directed through the injection module. The pressure differential across the purging fluid diminishes as fluid flows from the container; and when the pressure differential has decayed to about zero, a predetermined quantity of the fluid has flowed through the conduit and injection syringe. It has been found that the use of a purging volume aproximately 10 times the volume of the sample conduit and injection syringe consistently reduces the quantities of residual material in the system to extremely low levels.

Where excessively viscous liquids are being analyzed, the new system can be operated to provide an additional discharge of the accumulator into the sample container to provide a boost in the pressure differential across the conduit and the injection syringe during the purge. This boost in pressure increases the rate of the viscous fluid flow through the sample conduit and syringe. This capability helps insure that adequate purging volumes of relatively viscous sample fluids are obtained in a reasonable time.

Another important feature of the invention resides in the positioning of the injection syringe plunger during the purging process. In the preferred and illustrated embodiment of the invention the injection syringe is a side arm syringe and the projecting end of the syringe plunger is at least partially aligned with the side arm port in the syringe barrel so that purging fluid directed through the syringe impinges directly on the end of the plunger. This has the effect of scouring the plunger end to dislodge any remaining material While the system is being purged, the injection syringe directs the purging fluid into a drain system which retains the fluid and minimizes the amount of fluid vapor in the atmosphere, around the injection module. When purging has been completed, the injection syringe is operated to move the plunger of the syringe to a position at which a controlled dose of the sample liquid is disposed in the syringe, after which the syringe is removed from the drain and inserted into the analyzer inlet. The predetermined dose of the sample is then injected into the inlet for analysis.

After the purging cycle is completed but prior to the removal of the syringe from the waste system, the syringe plunger is advanced to a dosage stop to expel fluid from the syringe until the predetermined sample dose remains in the syringe. The syringe carriage is then operated to remove the syringe from the waste system and advance it into the analyzer. When the dosage stop element is moved out of the path of the plunger supporting member, the plunger can be driven into the syringe to inject the predetermined does into the analyzer.

Another feature of the invention is the provision of a sample analysis system wherein a control module governs the operation of the sample storage and injection modules and is capable of interrelating these operations with a computer. The system is constructed and arranged so that the entire analysis of multiple samples can be controlled by a programmed computer while at the same time permitting system operation by an operator.

Other features and advantages of the invention will be apparent from the following detailed description of a preferred embodiment made with reference to the accompanying drawings which form a part of the specification.

BRIEF DESCRIPTION OF THE DRAWINGS

FIG. 1 is a perspective view of a sample analysis system embodying the present invention with parts illustrated schematically;

FIG. 2 is a portion cross-sectional view of the side arm syringe;

FIG. 3 is a cross sectional view of part of a dipper tube assembly forming part of the storage module of FIG. 4 inserted in a sample container with parts broken away;

FIG. 5 is a schematic block diagram showing the interrelationship between components of a control module for the system as well as portions of the storage and injection modules.

DESCRIPTION OF A PREFERRED EMBODIMENT

Figure 4:
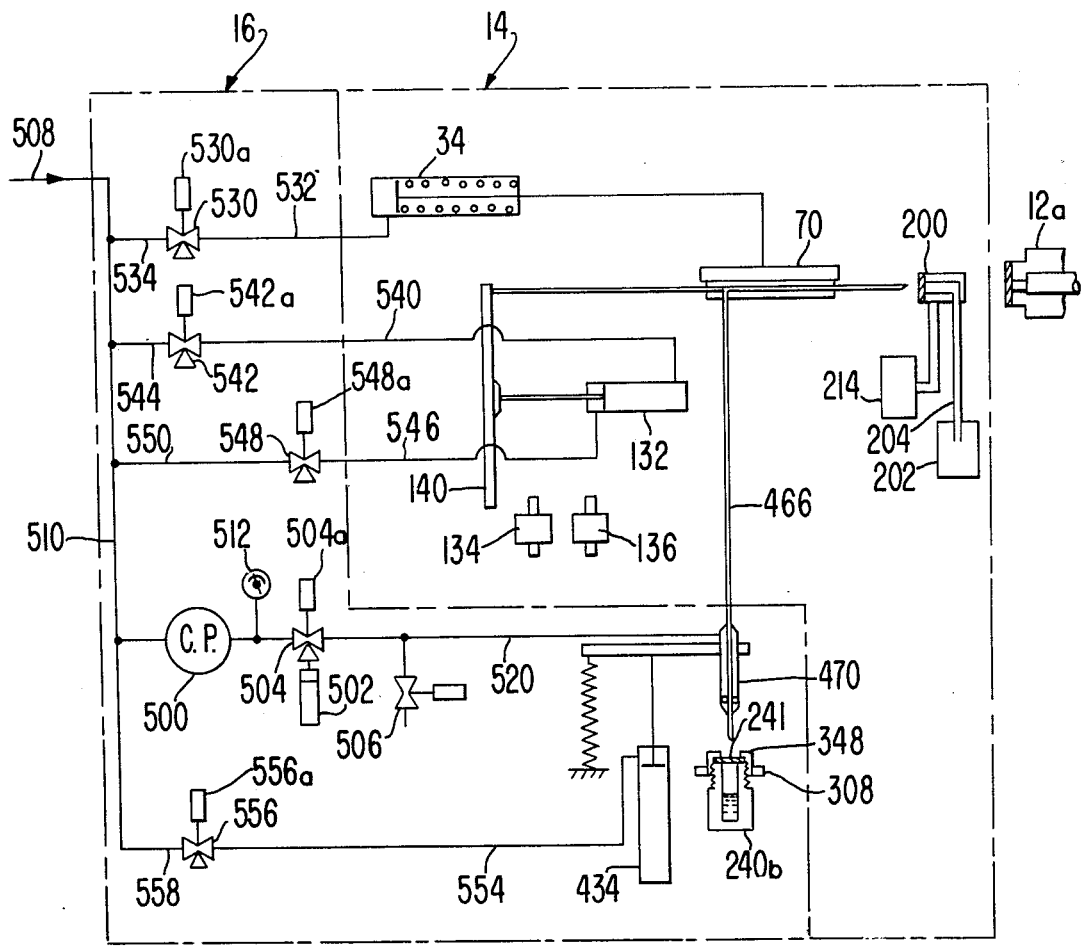
FIG. 4 is a schematic diagram of a fluid pressure system contained within the injection and storage modules.

An automatic sample analysis system 10 embodying the present invention is illustrated in FIG. 1 as comprising a sample analyzer 12, which may be, for example, an apparatus for analyzing a fluid sample by liquid or gas chromotography; a sample injection module 14 by which a sample of fluid to be analyzed is injected into the analyzer 12; a sample storage module 16 which houses a number of discrete samples of fluid to be analyzed and which supplies sample fluid to the injection module; a sample analysis computer 18 which is programmed to partially govern operation of the system and to receive raw data from the analyzer concerning the analysis of a given sample of fluid and to process that data into a desired useable form; a recorder 20 which is connected to the analyzer for producing graphic information concerning the analysis of given samples by the analyzer; and an electronic control module 22 which generally governs the operation of the remaining components of the system 10.

In brief, the system 10 operates in the following manner: The injection module 14 and the sample storage module 16 are connected to each other in a desired orientation, for example, in the orientation shown in FIG. 1, and are detachably connected to the analyzer 12, which may be of any suitable or conventional type or construction; and a number of containers of sample fluid are disposed in the storage module 16. Automatic operation of the system is then initiated by the operator, which results in a predetermined quantity of sample fluid from one container in the storage module 16 being extracted and delivered to the injection module 14 from which a predetermined quantity of the sample is injected into the analyzer 12. The analyzer 12 processes the sample fluid; and data resulting from the analyzer process is fed to the computer 18 and/or the recorder 20. At the same time, information concerning the identity of the sample injected into the analyzer 12 is supplied to a control module 22 from the storage module 16 and thence to the recorder 20 and computer 18 so that the data being obtained from the analyzer 12 is identified with the particular container from which the sample was removed. After the first fluid sample has been analyzed, sample fluid from a second container is directed from the storage module 16 to the sample injection module 14 and the analysis process is repeated. When all of the samples have been analyzed, the operation of the system 10 is automatically terminatable.

Prior to the injection of each fluid sample into the analyzer 12, the flow passageways through which the sample passes from the storage module 16 into the analyzer are purged to remove substantially all traces of the preceding sample fluid from the passages prior to the introduction of the next succeeding sample to the analyzer. Purging is conducted using the next succeeding sample fluid itself, or by using a suitable solvent and then the next succeeding sample, so that the possibility of contaminating any given fluid sample by the preceding sample or the solvent is minimized. The purging solvent is contained by the storage module 16 like the samples, and is introduced into the passages to be purged. The sequence of operation of the system 10 is governed by the control module 22 in cooperation with the computer 18.

It should be appreciated that the brief description of the operation of the system 10 has been simplified and generalized in order to provide an overall understanding of the functions and interrelationships of the various modules and components of the system 10. Certain components of the system 10 are described separately below.

FIG. 3 illustrates the needle assembly construction and the relationship between the needle assembly and the fluid container when the needle assembly has been forced into the container. The needle assembly 430 comprises a central tubular needle 460 having a bullet-nosed tip 462 for piercing the septum 241, and a central flow passageway 464. The central passageway communicates with a sample fluid conduit 466 which extends from the needle 460 to the side arm port of the injection syringe in the injection module. The passageway 464 opens into the container adjacent the tip 462 via ports 468 defined by a cross bore extending transversely through the needle. The ports are spaced from the tip so that they cannot core the septum and become blocked. When the needle assembly 430 is properly positioned in the container, the ports 468 are well below the level of the liquid in the container.

The needle 460 is surrounded by a second tubular needle 470 having a tapered end portion 472 fixed and sealed to the needle 460 at a location from the tip 462. The needle 470 defines a passageway 474 surrounding the needle 460, which communicates with the purging system and with the container via ports 478 formed by transverse holes extending through the wall of the needle 470. The needle 470 penetrates the container septum sufficiently that the ports 478 are located within the container. The ports 478 open transversely of the needle 470 to prevent coring of the septum.

With reference to FIG. 4, the purging system functions to force fluid from the container 240b and into the injection module by exposing the container to a controlled volume of gas at a predetermined pressure. The volume of gas at the predetermined pressure can be considered to possess a predetermined amount of purging energy proportional to the product of the pressure and the volume. The PV energy of the purging gas thus accurately determines the quantity of fluid which is directed to the injection module. The waste system tank 202 is maintained at atmospheric pressure throughout each purge cycle. As fluid is forced from the container to the injection module, the pressure in the container decays until the purging gas has expanded to a pressure about equal to atmospheric pressure.

As shown schematically by FIG. 4, the purging system comprises a pressure regulating valve 500, a pressure accumulator 502, an accumulator control valve 504 and a vent valve 506. The regulating valve 500 is connected to a source of pressurized gas by a supply conduit 508 and a pressure manifold 510 disposed in the storage module 16. The pressure source can be of any suitable or available construction and preferably provides air at pressures around 60 psig to the manifold 510 through the conduit 508 which extends into the module 16.

The regulating valve drops the supply pressure to a predetermined lesser pressure, e.g., 25 psig. The valve 500 can preferably be adjusted so that the controlled pressure can be varied as desired by the operator. A gauge 512 is associated with the valve 500 so that the magnitude of the controlled pressure can be monitored.

The accumulator 502 communicates with the regulating valve 500 via the control valve 504, which is a three-way solenoid operated valve having a small internal volume. The solenoid operator 504a is illustrated schematically and is operated from the control module 22. The control valve 504 has a first operating position in which the accumulator 502 communicates with the regulating valve 500 for charging the accumulator. This valve position is the "normal" valve position, and the accumulator is nearly continuously maintained in its charged state.

The accumulator 502 may be of any suitable or conventional construction and is not illustrated in detail. The accumulator preferably has a volume of about 100 microliters and, when charged, the accumulated gas is at a pressure of 25 psig. Because of the small accumulator volume, it can be rapidly charged from the regulator valve 500 when the control valve 504 is in its normal position.

The control valve solenoid 504a is operated from the control module 22 to a second valve position wherein communication between the accumulator and the regulating valve 500 is cut off and the accumulator communicates with the dipper tube needle 470 via a low internal volume conduit 520. This connection enables the accumulator to discharge into the unfilled gas volume of the fluid container and the connecting line volume via the needle 470. The accumulator discharge is relatively rapid, and equilibrates to an initial pressure Pi. After a few seconds, the control valve 504 returns to its normal position and the accumulator is recharged.

The initial pressure Pi is dependent upon a number of factors as indicated in equation (1), below $$Pr\, Vr + Ps\, VS = Pi\, (Vr + VS) \qquad \text{Eq. 1.}$$

For an accumulator volume Vr which is less than the unfilled gas volume of fluid container Vs, it is clear that the initial pressure Pi is very much dependent on Vs. The gas volume, or head space over the liquid, Vs in a 2000-microliter container will normally be permitted to vary from 250 to 1750 microliters. For example, if 250 microliters of solvent or sample is in the container, the head space will be 1750 microliters. Since one of the design objectives of this purging system is that it purge with a relatively constant amount of fluid even though the head space in the container vary from ⅛ to ⅞ of the container volume, it was necessary to devise a means whereby the volume of material purged is relatively constant over a wide range of head space and viscosities.

Applicants determined through experimentation that the utilization of a small charging accumulator volume as compared to the range of head space results in the optimum configuration. Preferably, the accumulator volume is disconnected from the container after charge. Considering steady state energy relationships for this configuration, it can be shown that for an isothermal condition:

$$Ps\, V_f = Pi\, Vs - Ps\, Vs \qquad \text{Eq. 2.}$$

(Energy out = Energy in − Energy remaining)
where
Pr = accumulator pressure prior to start of charge
Vr = accumulator volume
Vs = total gas volume of sample vial and hardware connecting to accumulator from sample vial
Ps = vial pressure at end of purge
Pi = initial pressure in vial after start of purge before liquid movement
$V_f$ = volume of solvent or sample flushed through the system.
For $$Ps = \frac{Pr}{3},$$

Eq. 2 has been solved and charted in Table I to show the relative independence of the amount of flush volume $V_f$ with respect to variation of the head space Vs.

TABLE I

| Vs | Pi | $V_f$ |
|---|---|---|
| 2Vr | 5/6 Pr | 3Vr |
| 15 Vr | 3/8 Pr | 15/8 Vr |

The Table I chart shows that for $2Vr < Vs < 15Vr$, it follows that $15/8\, Vr < V_f < 3\, Vr$.

In the preferred and illustrated system, the injection syringe has an internal volume of about 10 microliters and the sample conduit 466 has an internal volume of about 10 microliters. It has been found that purging such a system with a flow of fluid equal to about 10 times the combined syringe and conduit volumes reduces the quantity of residual material in the purge volume to consistently low levels, e.g., to less than 0.01% by volume. Accordingly, in the preferred system, the 100 microliter accumulator, charged to 25 psig, is effective to produce a purging volume of solvent and/or sample fluid of about 200 microliters.

As can be seen from Table I, with Vr = 100, in the steady state, $187 < V_f < 300$ microliters. Since the system operates with a convenient fixed purging time cycle which may be less than the equilibration time, it does not purge the full value shown by $V_f$. Therefore, normally at least 6 purge cycles can be run with a single 2-milliliter vial that has originally been filled to the 1750-microliter level, leaving a 250 microliter head space.

A method is known for moving calibrated amounts of fluid out of one container into another; and methods which employ a predetermined energy stored in a fixed volume at a fixed pressure as a prime mover are known. In such prior art methods, no attempts have been made to compensate for the unknown headspace volume in the sample container.

In these prior methods, the volume of an accumulator having an instantaneous pressure Pr was always made much larger than the unknown headspace volume of the sample vessel; and the effect of this headspace volume on the initial pressure in the accumulator at the start of the discharge of the accumulator into the sample vessel was minimal. In other words, Pr = Pi since Vr>>Vs. In order to make such schemes useful for moving very small amounts of fluid, Pr must be made very small. Since Vr is large, Pr must have a value very slightly above atmospheric pressure, or the system must be operated in a vacuum. Such systems require very expensive and precise pressure regulators, since even a slight change in pressure will result in a large change in Pr Vr. Furthermore, inherent in these earlier systems are the assumptions that the accumulator will discharge until its pressure equililbrates, and that the volume of the matter moved is given by the relationship:

(Instantaneous pressure—Initial pressure at start of discharge/Initial pressure at start of discharge)>(accumulator volume)

This equation does not take into consideration the resistance to flow of the more viscous solvents, or other significant energy losses in the system, such as losses due to surface tension, which can have large effects in small differential pressure systems. Therefore, with these methods known to the prior art, the pressure in the accumulator at the end of the discharge will not drop to the pressure at the start of the discharge. For the required lower pressure charge on the accumulator for small Pr Vr, a larger percentage of the energy is unavailable, depending on the viscosity and other physical characteristics of the sample fluid.

Some sample fluids have high vapor pressures at room temperature; and if the accumulator were discharged into a container of such a fluid, the partial pressure of the vapor combined with the Pr Vr energy of the purging gas could cause an excessive quantity of the fluid to be forced from the container. Accordingly, in the preferred embodiment of the invention, after the needle assembly has been inserted into a container, the vent valve 506 is opened to allow communication of the container with atmospheric pressure via the needle 470, the conduit 520 and the valve 506. The valve 506 is operated by a solenoid 506a which is energized and deenergized from the control module 22. In the normal sequence, when the vent 506 is operated the side arm of the syringe is closed.

After the vent valve 506 is opened to vent the container, it is reclosed and the container volume is substantially at atmospheric pressure. The control valve 504 is then actuated to discharge the accumulator into the container so that a predetermined controlled pressure differential is applied across the sample fluid, the fluid conduit, and the injection syringe. In the preferred embodiment of the invention, the control module functions to allot a one minute period during which purging is accomplished. Purging is normally completed within the alloted time.

Where a sample fluid has a relatively high viscosity, (e.g., greater than 1 cp), its flow resistance is relatively great and a single discharge of the accumulator may not provide sufficient energy for a complete purge during the alloted one minute purging period. In such circumstances, the operator can condition the control module to operate the control valve 504 to discharge the accumulator a second time during the purging period, e.g. after 30 seconds have elapsed. The additional Pr Vr energy thus supplied to the container compensates for the high fluid viscosity. After purging is completed, the dipper tube assembly is withdrawn from the container.

As illustrated by FIG. 4, the injection and storage modules 14, 16 are shown schematically by broken lines along with the various elements of the pneumatic system for operating the actuators in the modules.

As illustrated by FIG. 4, the injection syringe carriage actuator 34 communicates with a solenoid control valve 530 in the storage module by means of a conduit 532. The control valve 530 is in turn connected to the pressure manifold 510 by a conduit 534. The valve solenoid 530a is energized and deenergized from the control module 22 to control operation of the valve. When the actuator 34 is operated to advance the syringe carriage towards the analyzer inlet 12a or the waste receptacle, the valve 530 is operated to direct high pressure air to the actuator 34. The carriage is retracted by operating the valve 530 to vent the actuator 34 so that the actuator return spring retracts the carriage.

The double acting plunger actuator 132 communicates with the manifold 510 at one end via a conduit 540, a control valve 542 an a conduit 544. The opposite end of the actuator 132 communicates with the manifold via a conduit 546, a control valve 548 and a conduit 550. The valves 542 and 548 each are operated by solenoids 542a, 548a which are wired to the control module. The valves 542, 548 are constructed like the valve 530 to either supply high pressure air to their respective ends of the actuator 132 or to vent the actuator, depending on energization of the solenoids. When both valves direct pressurized air to the actuator 132, the plunger is positively positioned by the actuator, as noted previously. This operation of the valves only occurs when the cross bar 140 engages one or the other of the dosage stops 134, 136, which are schematically illustrated in FIG. 4, to enable retraction of the dosage stop element.

The single acting dipper tube actuator 434 is communicable to the manifold 510 via a conduit 554, a control valve 556 and a conduit 558. The control valve 556 includes a solenoid 556a wired to the control module 22. The valve 556 is constructed and functions the same as the valve 530.

As is apparent from FIG. 4, the pressure conduits 532, 540 and 546, as well as the sample fluid conduit 466, all extend between the storage and injection modules. Additionally, as noted above, the electric conductors for the dosage stops 134, 136 and the waste system solenoid 214 also extend from the storage module to the injection module.

FIG. 5 schematically shows the functional interrelationships of the components of the electronic control module 22 as they are related to the remaining components of the system 10. For convenience, the overall operation of the system 10 is described in reference to FIG. 5.

For the purpose of the ensuing description, it is assumed that up to four sample container traps have been loaded into the storage module, with the containers or vials being arranged so that the sample and solvent containers are in a desired sequence proceeding around the turntable; that the container pocket at the extraction station is empty; and that the system 10 is interfaced with a computer 18 which is programmed merely to process data produced by the analyzer 12 rather than to control the overall operation of the system 10.

The control module 22 is provided with a front panel (not illustrated) for switches and displays which are accessible to the operator. To initiate operation of the system 10, the operator depresses a front panel "power" switch button associated with circuitry 580 which functions to supply low voltage power to logic circuitry in the control module.

The operator then depresses a "computer enable" switch button associated with circuitry 584 to enable operation of the computer; and a "temperature program enable" switch button is associated with circuitry 586. When an instrument such as a gas chromotograph is employed in the system, certain temperature conditions must be established in the instrument before it can be used to analyze samples. The temperature program enabling circuitry 586 enables these conditions to be sensed and, when these conditions have been established, provides a signal to the logic circuitry 582 to enable further operation of the system 10.

Likewise, the computer enabling circuitry 584 enables the computer to signal the logic circuitry 582 when the computer is conditioned to proceed.

When both the computer and the analyzer are enabled, the operator depresses a "ready" switch buttom associated with circuitry 590 which enables the supply of higher voltage power for operating the solenoids and the recorder from a power supply 592. The power supply 592 supplies power to the solenoids in the injection and storage modules via solenoid driver circuitry 594 which comprises individual solenoid control switches. The power control 592 also functions to enable the recorder through a recorder controlling switch (not illustrated).

Sample volume selecting circuitry 596 governs which dosage stop in the injection module will be operated during the analysis cycles. The circuitry includes front panel switches by which the operator can select the desired sample dosage. When one of the switches is actuated, a sequence controlling circuit 600 is conditioned to effect operation of the selected dosage stop at appropriate times during the operation of the system.

The system 10 is capable of injecting repeated doses of each sample fluid into the analyzer for successive separate analysis of each dose. An "injection per container" circuit 602 and an injection counter circuit 604 cooperate with the logic circuitry 582 to enable this function. The circuitry 602 includes several selector switches on the front panel; and it is assumed, for the purpose of this description, that the operator actuates the switch indicating a single injecton per container.

At this juncture, the system 10 is ready to be operated to analyze samples. The samples can be analyzed one at a time under the control of the operator such that in order to analyze each successive sample the operation of the system must be manually initiated by the operator. Alternatively, the system can be conditioned to automatically analyze each successive sample without requiring operator assistance.

Run circuitry 610 cooperates with the logic circuitry 582 to control whether the system operates automatically or not. The run circuitry 610 includes selector switches labeled "single" and "multi"; and it is assumed that the operator actuates the "multi" selector switch so that all of the samples in the storage module will be automatically analyzed.

Since the pocket at the storage module extraction station is empty, the logic circuitry 582 provides an operating signal to a turntable motor control circuit 612 which in turn initiates operation of the turntable drive motor 340 via a bidirection motor driver 614. The motor 340 drives the turntable until a sample container is sensed at the extraction station by the microswitch 382. The signal produced by the microswitch 382 is transmitted to a decoder circuit 616, from which the signal is transmitted to both the logic circuit 582 and the sequence control circuit 600. The logic circuit functions to enable the sequence control circuit to proceed while the signal from the decoder 616 to the sequence control circuit conditions the sequence control circuit to enable both a purge and an injection of the sample fluid.

The sequence control circuitry 600 next functions to cause the system components to perform the following steps:

1. The syringe carriage 70 is advanced to thrust the needle 94 into the waste receiver 200;
2. The actuator 132 for the plunger 92, which is initially in its fully depressed position, is subjected to fluid pressure to urge the plunger toward the depressed position;
3. The dipper tube assembly 430 is thrust into the sample container at the extraction station;
4. The container vent valve 506 is opened to vent vapor pressure from the container;
5. The vent valve 506 is reclosed;
6. The accumulator control valve 504 is operated to discharge the accumulator into the container;
7. The syringe plunger actuator 132 is operated to withdraw the plunger 92 to the side arm port;
8. A dwell period is provided during which purging of the sample conduit 466 and the syringe assembly 72 is completed;
9. The dipper tube assembly is raised from the container:
10. A dosage stop solenoid is energized to provide a preset dosage stop;
11. The plunger 92 is depressed to the dosage stop, thus closing the syringe side arm port;
12. The syringe carriage is retracted to withdraw the needle 94 from the waste receiver;
13. The waste receiver is actuated to its retracted position;
14. The carriage 70 is advanced to thrust the needle 94 into the analyzer inlet 12a;
15. The pressure across the piston of the plunger actuator 132 is equalized;
16. The dosage stop solenoid is deenergized to retract the stop element;
17. The plunger 92 is driven into the syringe barrel to its limit of travel;
18. The syringe carriage 70 is retracted to withdraw the needle from the analyzer inlet;
19. The waste receiver 200 is repositioned between the needle 94 and the analyzer inlet;
20. The plunger actuator is deenergized.

Each of the enumerated steps occurs immediately after the preceding step, except for steps 6 and 10 which preferably require a four second delay prior to the succeeding step. This is due to the time required to completely discharge the accumulator; and each time the control valve 504 is actuated to discharge the accumulator, the delay period follows.

The time delay periods are determined by a clock circuit 620 which provides timed pulses to the sequence control circuit 600.

When a viscous sample fluid is to be injected, the operator can enable a high viscosity circuit 622 which conditions the sequence control circuit 600 to discharge the accumulator into the container a second time during the dwell period of step 8.

When the sample is actually injected into the analyzer, the sequence control circuit 600 sends an appropriate confirmatory signal.

When the fluid is injected, the sequence control circuit provides a signal to the logic circuitry 582, the injection counter 604, an analysis time clock circuit 630, an auxiliary time clock circuit 632, the recorder 20, and to an integrator associated with the recorder.

The logic circuitry 582 initiates operation of the computer via the enabling circuitry 584 so that data from the analyzer is processed by the computer. The injection counter receives and stores the injection signal for comparison with the required number of injections per container selected by the circuitry 602. The signal to the recorder results in an injection mark being placed on the graph produced by the recorder.

The integrator is a device which integrates the area under the curve produced by the recorder, and may be used along with a computer. In some installations where a computer is not available, an integrator is used in place of the computer. The integrator is operated by the injection signal so that it is immediately operative as the recorder begins to produce the analysis results.

The analysis time clock circuit 630 receives timing pulses from the clock circuit 620 and governs the length of the analysis period. The length of the analysis time is preset by the operator via a time controlling circuit 634. The operator can preset the time by two dial switches graduated in tens and units of minutes.

When the injection signal is received by the analysis clock circuit 630, it begins to time out.

The time clock circuit 630 provides one output to the logic circuit 582 and another output to a display control circuit 636. When the analysis time clock circuit has timed out, the output to the logic circuit causes termination of the first sample analysis cycle and enables analysis of the next succeeding sample. The output to the display control 636 enables the elapsed analysis time to be displayed on the front panel by a display circuit 638. The operator can cause the elapsed time to be displayed by depressing an elapsed time button forming part of a display selecting circuit 640.

The auxiliary time clock circuit 632 is associated with an auxiliary device controlling circuit 642 which governs operation of auxiliary devices, such as valves in the analyzer. In some circumstances it may be desired to change one or more physical conditions, such as temperature, in the analyzer at a predetermined time during the analysis. the auxiliary device is operated from the circuit 642 and the time clock circuit 632 to effect the desired change in condition. The operator controls the time during the analysis when the auxiliary device operates by a time controlling circuit 644, which is identical in function and construction to the circuit 634 described above.

When the sample container is first located at the extraction station, the microswitches 401–408 are appropriately actuated to produce a binary signal representing the tray or rack identity and the location of the container in that tray. The switches are shown schematically and out of position in FIG. 5 for the purpose of this description. The output from the switch is directed to a decoder circuit 650 which in turn has an output to the computer, an output to a printer of the recorder, and an output to the display control circuit 636. When an injection has been made and operation of the computer and the recorder is initiated, as described, the output from the decoder 650 cause the container and tray numbers to be printed on the output data from the recorder and computer. The container and tray numbers can also be displayed on the front panel when the operator depresses a display button forming part of the circuit 640. The operator can thus immediately determine the identity of the sample container being analyzed.

When the analysis of the first sample is completed, the analysis time clock circuit 630 signals the logic circuit 582, which in turn initiates another cycle by causing the motor 340 to operate so that the next container is moved to the extraction station 250. Assuming the next container is a solvent container, this fact is sensed by the microswitch 384 and then sent to the container decoder, and an appropriate signal is supplied to the logic and sequence control circuits. The sequence control circuit operates the system through steps 1–9 enumerated above, after which the logic circuitry is supplied with a signal indicating the end of a cycle.

The logic circuitry then initiates a succeeding cycle by causing the next succeeding container to be moved to the extraction station. The various cycles are repeated until the final container in the storage module is sensed. The decoder circuit 616 provides a final container signal to the logic circuit so that after the final sample is analyzed the system is automatically shut down.

Some analyzers, particularly gas chromotographs, become unstable if their electrical power supplies are interrupted for any length of time. Generally, if a power outage occurs which is shorter than 10 seconds in duration, the analyzer can be stabilized rather promptly. A power failure circuit 652 is provided in the control module for sensing a power failure, timing the duration of the failure, and providing appropriate control signals to the logic circuitry 582. When a power failure is sensed, operations of those components of the system directly related to analysis of a sample are suspended (e.g., the analysis and auxiliary time clock circuits, the computer, the integrator and the recorder). If the power failure has a duration of less than a predetermined period, e.g., 10 seconds, the power failure circuit 652 governs the logic circuitry so that the operation of the system components remains suspended for a predetermined period of time during which the analyzer is restabilized. The analysis is thereafter enabled to proceed. If the power failure has a duration of more than 10 seconds, the power failure circuit provides a signal to the logic circuit which causes the entire system to shut down. When power is restored the operator must restart the system to continue the analysis procedure.

The system 10 is adapted to be completely controlled by an appropriately programmed computer. To place the system under the operation of the computer, the computer enable circuitry 584 is operated and the injections per container circuit 602 and the sample volume control circuit 596 are conditioned for computer control by the actuator of respective switches marked "C" in these circuits. The computer can be programmed to operate the storage module turntable to seek out desired samples (aided by the decoder circuit 650), govern the operation of the sequence control circuitry 600, independently time out the analysis period to complete the analysis, and proceed on to another sample container.

Some analyzers have two analyzer inlet ports; and with such an analyzer it is possible to provide an injection module 14, a storage module 16 and a control module 22 for each inlet port. The operation of these separate units can be interrelated by interconnecting the logic circuits of each control module as shown by the lines 654, 655 of FIG. 5. This interconnection allows one unit to be readied for an injection while a sample from the other unit is being analyzed, and vice versa.

While a single embodiment of the present invention has been illustrated and described in considerable detail, the invention is not to be considered limited to the precise construction shown. Numerous adaptations, modifications and uses of the invention may occur to those skilled in the art to which the invention relates, and it is the intention to cover all such adaptations, modifications and uses which fall within the scope or spirit of the appended claims.

We claim:
1. An automatic injection apparatus comprising a side arm syringe and means for purging said syringe with a liquid, said syringe purging means comprising:
   a. a closed container for holding said liquid, said container in operation having a head space above said liquid;
   b. a first conduit extending in operation into said container and defining a first port opening into said liquid, said first conduit communicating through a side port of said syringe with a fluid receiver;

c. means for preventing communication between said first conduit and said fluid receiver;

d. a second conduit extending in operation into said container and defining a second port opening into said head space;

e. means for providing a controlled quantity of purging liquid through said syringe, said controlled quantity of purging liquid being adequate to purge said syringe irrespective of the head space volume and the viscosity of said liquid, said means for providing said controlled quantity of purging liquid comprising an accumulator for storing a predetermined volume of gas at a predetermined pressure, the volume of said accumulator being less than the volume of said head space, and said predetermined pressure exceeding the pressure at said fluid receiver by a predetermined amount;

f. means for providing a gas supply to said accumulator;

g. means for providing communication from said accumulator to said second conduit; and h. first and second valves, said first valve being selectively operable and having a first state for providing communication from said gas supply means to said accumulator for charging said accumulator, and a second state for providing communication from said accumulator to said second conduit, said second valve being connected to said second conduit and said first valve, said second valve having a first state for providing communication from said container to atmospheric pressure via said second conduit and a second state for permitting communication from said first valve to said second conduit, whereby in said second state of both said first and second valves said gas discharges from said accumulator into said head space.

2. The apparatus of claim 1 wherein said container is closed by a septum and said first and second conduits comprise concentric needle-like members, said first conduit defining a tip for piercing said septum and said first port comprising an opening extending transversely through the wall of said first conduit adjacent said tip, said second conduit surrounding said first conduit at a location spaced from said tip and said second port extending transversely through the wall of said second conduit for establishing communication to said head space.

3. The apparatus of claim 1 wherein said first and second valves are actuatable by solenoid means.

4. The apparatus of claim 1 further comprising means for analyzing said liquid, and means for actuating said syringe to inject said liquid into said analyzing means.

5. The apparatus of claim 4 wherein said means for actuating said syringe is gas-pressure actuatable.

6. The apparatus of claim 5 wherein said means for actuating said syringe comprises a cylindrical chamber communicable at either end to a source of pressurized gas, a plunger moveable within said chamber in response to the direction of entry of pressurized gas into said chamber, said plunger having a shaft extending outside said chamber, sand a cross bar connected both to said shaft and to said syringe whereby the amount of liquid injected from said syringe is related to the extent of movement of said cross bar.

7. The apparatus of claim 6 further comprising a dosage stop for engaging said cross bar, thereby limiting the amount of liquid injected from said syringe.

8. An automatic injection apparatus comprising a side arm syringe and means for purging said syringe with a liquid, said syringe purging means comprising:

a. means for supporting a container for holding said liquid, said container in operation having a head space above said liquid, said head space being pressurized to a pressure higher than atmospheric pressure;

b. a first conduit, said first conduit in operation being extendible into said container and defining a first port opening into said liquid, said first conduit in operation being communicable through a side port of said syringe with a fluid receiver;

c. means for preventing communication between said first conduit and said fluid receiver;

d. a second conduit, said second conduit in operation being extendible into said second container and defining a second port opening into said head space;

e. means for providing a controlled quantity of purging liquid through said syringe, said controlled quantity of purging liquid being adequate to purge said syringe irrespective of the head space volume and the viscosity of said liquid, said means for providing said controlled quantity of purging liquid comprising an accumulator for storing a predetermined volume of gas at a predetermined pressure, the volume of said accumulator being less than the volume of said head space, and said predetermined pressure exceeding the pressure at said fluid receiver by a predetermined amount;

f. means for providing a gas supply to said accumulator;

g. means for providing communication from said accumulator to said second conduit; and h. first and second valves, said first valve being selectively operable and having a first state for providing communication from said gas supply means to said accumulator for charging said accumulator, and a second state for providing communication from said accumulator to said second conduit, said second valve being connected to said conduit and said first valve, said second valve having a first state for providing communication from said container to atmospheric pressure via said second conduit and a second state for permitting communication from said first valve to said second conduit, whereby in said second state of both said first and second valves said gas discharges from said accumulator into said head space.

9. A method of purging a side arm syringe in an apparatus for injecting sample liquid into an analyzer, said syringe comprising an elongate chamber having a side arm port and exit port, a plunger being disposed for movement within said chamber, said method comprising the steps of:

a. moving said plunger to a position at which said side arm port and said exit port are not in liquid communication;

b. providing liquid communication through a conduit between said side arm port and a source of purging liquid, said source of purging liquid being an enclosed container having a head space above said liquid;

c. venting said head space to atmospheric pressure;

d. establishing a pressure differential between said head space over said purging liquid and said exit port by placing said head space in pressure communication with a predetermined volume of gas at a predetermined pressure, said predetermined volume being smaller than the volume of said head space, and e. permitting communication between said head space and said exit port, whereby a controlled quantity of said purging liquid is directed through said syringe, said controlled quantity of purging liquid being adequate to purge said syringe irrespective of the head space volume and the viscosity of said liquid.

10. The method of claim 9 wherein the step of establishing a pressure differential between said purging liquid and said exit port comprises providing communication between said head space and said predetermined volume of gas at a higher pressure than the pressure at said exit port for a time sufficient to equilibrate the pressure in said head space, and thereafter disconnecting said head space from said predetermined volume of gas.

11. The method of claim 9 for purging said syringe with a more viscous liquid, said method comprising the additional steps of placing said head space in pressure communication with said predetermined volume of gas for a time sufficient to equilibrate the pressure in said head space for a second time, after disconnecting said head space from said predetermined volume of gas, and then permitting said gas in said head space to move said purging liquid to said exit port.

12. The method of claim 9 wherein the volume of purging liquid directed through said syringe is approximately ten times the combined volume of said syringe and said conduit between the side arm port of the syringe and the source of purging liquid.

* * * * *

UNITED STATES PATENT AND TRADEMARK OFFICE
CERTIFICATE OF CORRECTION

PATENT NO. : 3,954,012
DATED : May 4, 1976
INVENTOR(S) : Urs Christen, Raymond E. Pecsar, Brent E. Wadsworth It is certified that error appears in the above-identified patent and that said Letters Patent are hereby corrected as shown below:

Column 1, line 39:      Change "tack" to --task--.
Column 2, line 10:      Change "is" to --was--.
Column 2, line 19:      Change "extending" to --expending--.
Column 2, line 24:      After "were" insert --analyzed--.
Column 3, lines 53-62:  Delete.
Column 3, line 66:      Delete ",".
Column 4, line 15:      Change "does" to --dose--.
Column 5, line 34:      After "analyzer" insert --12--.
Column 5, line 39:      After "sample" insert --fluid--.
Column 6, line 5:       After "location" insert --spaced--.
Column 8, line 47:      Change "equililbrates" to --equilibrates--.
Column 9, line 56:      Change "an" to --and--.
Column 10, line 24:     Change "traps" to --trays--.
Column 10, line 57:     Change "buttom" to --button--.
Column 12, line 2:      Change ":" to --;--.
Column 14, line 24:     After "restored" insert --,--.
Column 15, line 65:     Change "sand" to --and--.
Column 16, line 45:     After "said" insert --second--.
Column 18, line 11:     Change "after" to --thereafter--.

Signed and Sealed this

Twentieth Day of July 1976

[SEAL]

Attest:

RUTH C. MASON
*Attesting Officer*

C. MARSHALL DANN
*Commissioner of Patents and Trademarks*

UNITED STATES PATENT AND TRADEMARK OFFICE
CERTIFICATE OF CORRECTION

PATENT NO. : 3,954,012
DATED : May 4, 1976
INVENTOR(S) : Urs Christen, Raymond E. Pecsar, Brent E. Wadsworth It is certified that error appears in the above-identified patent and that said Letters Patent are hereby corrected as shown below:

Column 16, line 20: Delete "second".

Signed and Sealed this

Ninth Day of November 1976

[SEAL]

Attest:

RUTH C. MASON
Attesting Officer

C. MARSHALL DANN
Commissioner of Patents and Trademarks